United States Patent
Perry (10) Patent No.: US 9,603,611 B2
(45) Date of Patent: Mar. 28, 2017

(54) INTERBODY SPACER AND PLATE INSERTER AND METHODS OF USE

(71) Applicant: Alphatec Spine, Inc., Carlsbad, CA (US)

(72) Inventor: Thomas F. Perry, Vista, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 170 days.

(21) Appl. No.: 14/155,301

(22) Filed: Jan. 14, 2014

(65) Prior Publication Data

US 2014/0316419 A1   Oct. 23, 2014

Related U.S. Application Data

(60) Provisional application No. 61/752,802, filed on Jan. 15, 2013.

(51) Int. Cl.
| | |
|---|---|
| *A61B 17/70* | (2006.01) |
| *A61B 17/17* | (2006.01) |
| *A61B 17/80* | (2006.01) |
| *A61F 2/44* | (2006.01) |
| *A61F 2/46* | (2006.01) |
| *A61F 2/30* | (2006.01) |

(52) U.S. Cl.
CPC ...... *A61B 17/1728* (2013.01); *A61B 17/1757* (2013.01); *A61B 17/808* (2013.01); *A61F 2/4455* (2013.01); *A61F 2/4465* (2013.01); *A61F 2/4611* (2013.01); *A61F 2002/30785* (2013.01); *A61F 2002/4475* (2013.01); *A61F 2002/4623* (2013.01)

(58) Field of Classification Search
CPC ... A61B 17/70; A61B 17/1728; A61B 17/808; A61F 2/4465
USPC .... 606/86 A, 99, 280–299; 623/17.11–17.16
See application file for complete search history.

(56) References Cited

U.S. PATENT DOCUMENTS

| | | | |
|---|---|---|---|
| 6,730,127 B2* | 5/2004 | Michelson | A61F 2/442 606/247 |
| 2012/0265259 A1* | 10/2012 | LaPosta | A61B 17/8894 606/86 A |
| 2012/0310293 A1* | 12/2012 | Refai | A61F 2/4611 606/86 R |

* cited by examiner

*Primary Examiner* — Christopher Beccia
(74) *Attorney, Agent, or Firm* — John Chau (57) ABSTRACT

An attachment guide for an interbody cage and a spinal plate includes a guide body and a coupling element. The guide body includes a proximal end, a pair of flanges, and a distal end. The proximal end includes an inserter attachment element configured to removably receive an inserter instrument. The pair of flanges extends from the guide body and is configured to engage the spinal plate. The distal end includes a surface configured to contact an anterior surface of the interbody cage and a cage engagement element configured to extend distally from the surface and into a wall of the interbody cage. The coupling element extends through an aperture of the guide body from the proximal end to the distal end and is configured to draw the pair of flanges into greater contact with the spinal plate and the cage engagement element into greater contact with the interbody cage.

15 Claims, 7 Drawing Sheets

INTERBODY SPACER AND PLATE INSERTER AND METHODS OF USE

CROSS-REFERENCE TO RELATED APPLICATIONS

The present application claims priority to U.S. Provisional Application Ser. No. 61/752,802 entitled "Interbody Spacer and Plate Inserter and Methods of Use" which was filed on Jan. 15, 2013 and is incorporated herein by reference in its entirety.

FIELD

The present invention generally relates to the field of spinal orthopedics, and more particularly to methods and systems for inserting aligned interbody cages and plates into the intervertebral space.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

When one or more disks degenerate through accident or disease, nerves passing near the affected area may be compressed and are consequently irritated. The result may be chronic and/or debilitating back pain. Various methods and apparatus have been designed to relieve such back pain, including spinal fusion using an interbody spacer or suitable graft using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in these techniques, also commonly referred to as vertebral body replacements (VBR) devices, are placed in the interdiscal space between adjacent vertebrae of the spine. Many times an exterior plate is used in conjunction with the VBR to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

One significant challenge to providing fusion stability (prior to actual bone ingrowth fusion) is preventing spinal extension during patient movement. Distraction of the vertebral space containing the fusion graft may cause the interbody spacer to shift or move disrupting bone ingrowth fusion and causing pain. An exterior plate is often used with the interbody spacer to hold the adjacent vertebrae while the fusion occurs.

Currently, a surgeon is limited to using his or her line of sight to align the interbody cage and plate. There remains a need for an attachment guide for aligning an interbody spacer and an anterior cervical plate during insertion and implanting in a patient.

SUMMARY

Accordingly, provided herein are systems and methods of use related to an attachment guide for maintaining proper alignment of an interbody spacer or cage and an anterior spinal plate during insertion and implantation.

An attachment guide for aligning an interbody cage and a spinal plate during insertion includes a guide body and a coupling element. The guide body includes a proximal end, a pair of flanges, and a distal end. The proximal end includes an inserter attachment element configured to removably receive an inserter instrument. The pair of flanges extends from the guide body and is configured to engage the spinal plate. The distal end includes a surface configured to contact an anterior surface of the interbody cage and a cage engagement element configured to extend distally from the surface and into a wall of the interbody cage. The coupling element extends through an aperture of the guide body from the proximal end to the distal end and is configured to draw the pair of flanges into greater contact with the spinal plate and the cage engagement element into greater contact with the interbody cage.

In other features, a locking pin extends partially into the aperture and is configured to engage the coupling element to prevent removal of the coupling element from the aperture. The inserter attachment element comprises an externally threaded projection. The pair of flanges includes a distal projecting lip configured to extend partially around a lateral portion of the spinal plate. The surface of the distal end is contoured to engage a curved anterior surface of the interbody cage. The cage engagement element comprises a pair of engaging prongs configured to extend into alignment apertures of the interbody cage.

In still other features, the aperture for receiving the coupling element is disposed along a longitudinal axis of the guide body and a second aperture is disposed orthogonal to and partially intersecting the first aperture, such that when the screw and a locking pin are inserted into the first and second apertures the screw is captured within the body component by the locking pin. The screw further comprises a head portion, a smooth central portion, and a threaded portion.

In yet other features, the attachment guide may be used in combination with an inserter instrument. The inserter instrument includes an outer shaft and an inner shaft. The outer shaft includes a distal end configured to engage the inserter attachment element and a proximal end with a first handle portion to attach the inserter instrument to the attachment guide. The inner shaft extends through the outer shaft and includes a distal end configured to engage the coupling element and a proximal end with a second handle portion to actuate the coupling element. The distal end of the outer shaft includes an internal thread and the distal end of the inner shaft includes a drive bit.

An attachment guide for aligning an interbody cage and a spinal plate during insertion includes a guide body, a coupling element, and a locking pin. The guide body includes a proximal end, a pair of flanges, and a distal end. The proximal end includes an externally threaded projection configured to removably receive an inserter instrument. The pair of flanges extends from the guide body and is configured to extend partially around a lateral portion of the spinal plate. The distal end includes a contoured surface configured to contact a curved anterior surface of the interbody cage and a cage engagement element including a pair of engaging prongs configured to extend distally from the surface and into alignment apertures in a wall of the interbody cage. The coupling element extends through an aperture of the guide body and includes a proximal head portion with a drive bit recess, a smooth central portion, and a threaded distal portion configured to threadably engage the wall of the interbody cage. The locking pin extends partially into the aperture and is configured to engage the smooth central portion of the coupling element to prevent removal of the coupling element from the aperture.

In other features, actuation of the coupling element draws the pair of flanges into greater contact with the spinal plate and the pair of engaging prongs into greater contact with the interbody cage. The attachment guide may be used in combination with an inserter instrument including an outer shaft and inner shaft. The outer shaft includes a distal end configured to engage the inserter attachment element and a proximal end with a first handle portion to attach the inserter instrument to the attachment guide. The inner shaft extends through the outer shaft and includes a distal end configured to engage the coupling element and a proximal end with a second handle portion to actuate the coupling element. The distal end of the outer shaft comprises an internal thread and the distal end of the inner shaft comprises a drive bit.

A system for pre-aligning a spinal plate with an interbody cage during insertion includes an alignment guide and an inserter instrument. The alignment guide includes a guide body, a coupling element, and a locking pin. The inserter instrument includes an outer shaft and an inner shaft.

The guide body includes a proximal end with an externally threaded projection configured to removably receive the instrument, a pair of flanges extending from the guide body configured to extend partially around a lateral portion of the spinal plate, and a distal end including a contoured surface configured to contact an curved anterior surface of the interbody cage and a cage engagement element comprising a pair of engaging prongs configured to extend distally from the surface and into alignment apertures in a wall of the interbody cage.

The coupling element extends through an aperture of the guide body and includes a proximal head portion with a drive bit recess, a smooth central portion, and a threaded distal portion configured to threadably engage the wall of the interbody cage.

The locking pin extends partially into the aperture and is configured to engage the smooth central portion of the coupling element to prevent removal of the coupling element from the aperture.

The outer shaft includes a distal end with an internal thread to engage the externally threaded projection and a proximal end with a first handle portion to attach the inserter instrument to the attachment guide The inner shaft extends through the outer shaft and includes a distal end with a drive bit to engage the drive bit recess and a proximal end with a second handle portion to actuate the coupling element.

BRIEF DESCRIPTION OF THE DRAWINGS

FIG. 9a is cross sectional view of FIG. 1 attachment guide without the screw or pin inserted taken from directional line 9a-9a, FIG. 9b is a front cross sectional view of FIG. 9a;

FIG. 10c is an end view of the drill guide component of FIG. 10a;

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 1:
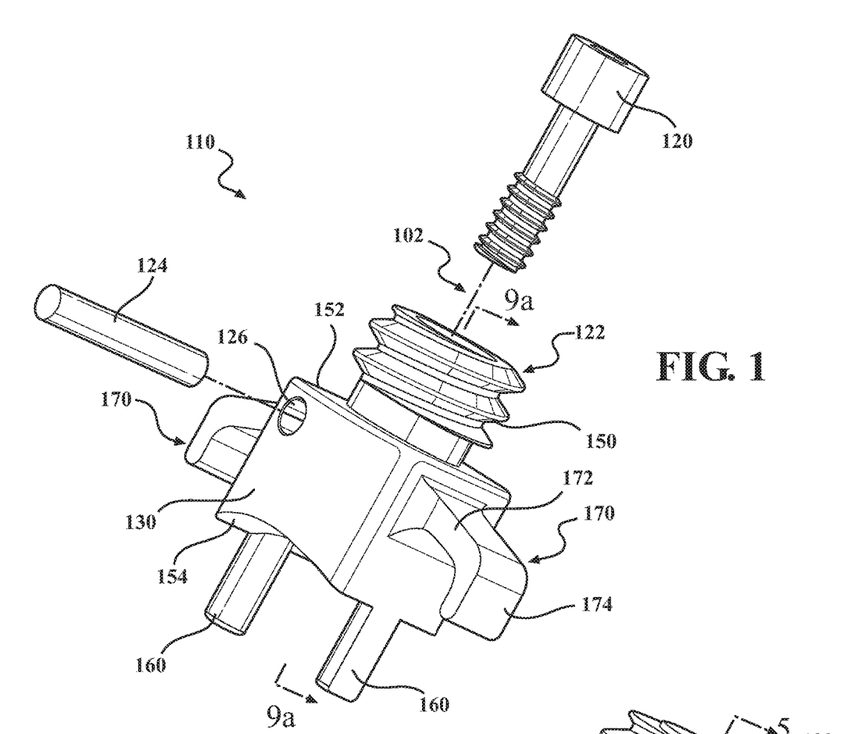
FIG. 1 is an exploded view of one embodiment of the attachment guide.
Figure 2:
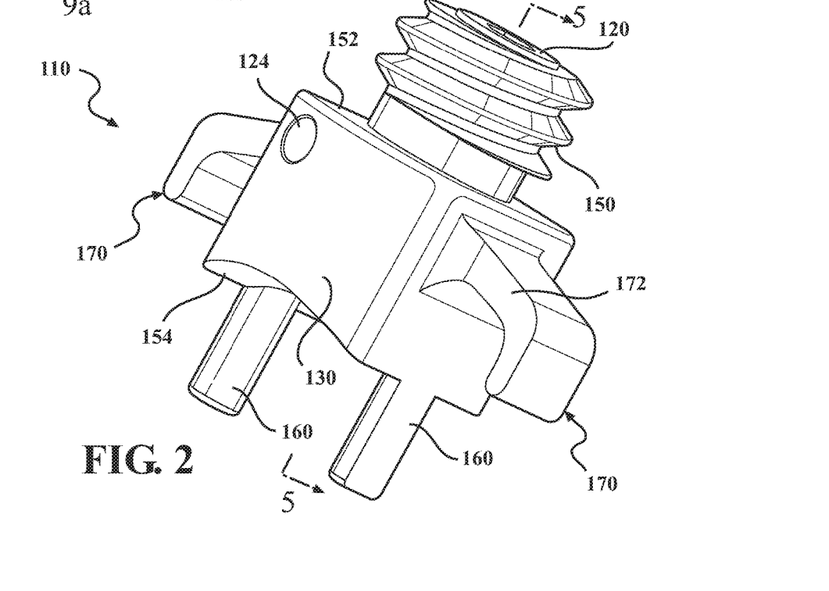
FIG. 2 is an assembled view of one embodiment of the attachment guide.
Figure 3:
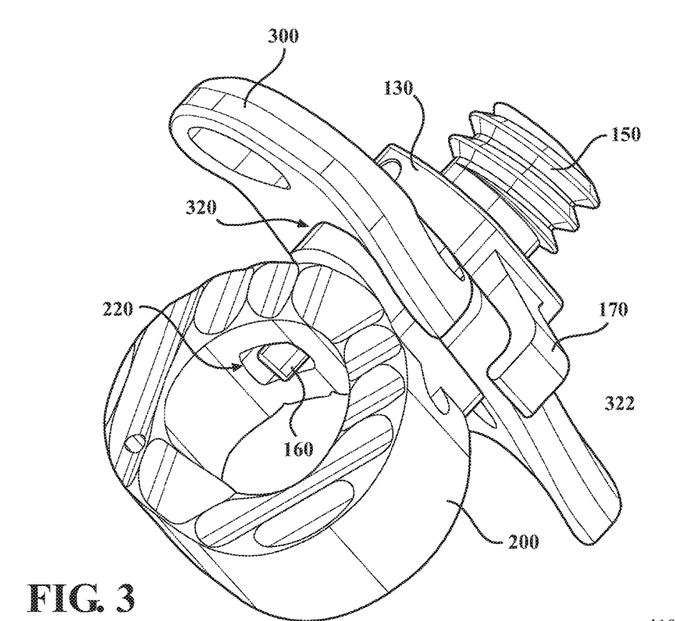
FIG. 3 is an isometric view of one embodiment of the attachment guide mated with an interbody cage and an anterior cervical plate.

FIG. 1 illustrates an exploded view of an exemplary attachment guide 110 of the present invention. The attachment guide 110 is generally comprised of a body component 130, a screw 120, a driver attachment element 150, and a pin 124. In many embodiments, the body component 130 is generally cube shaped. Alternatively, the body component 130 may be generally polygonal shaped, circular-shaped, rectangular-shaped, and the like. The attachment guide 110 may have different sizes and/or configurations of components depending on a particular interbody and plate, a given guide 110 is designed to work with. Generally, however, any size interbody 200 and plate 300 may be used with a given attachment guide 110, as shown in FIGS. 2 and 3. Generally, the attachment guide 110 may be made from any suitable biocompatible material as known in the art including, by way of example and not limitation, stainless steel, silicone, shape memory metals and polymers, thermoplastic or other materials.

Figure 5:
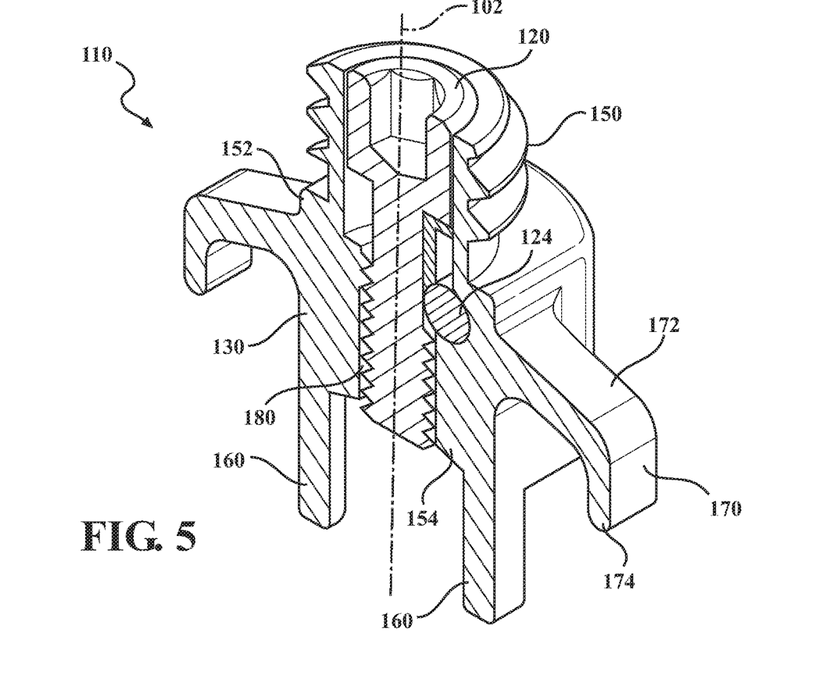
FIG. 5 is a cross sectional isometric view of one embodiment of the attachment guide, with the screw and pin inserted so as to lock the screw within the attachment guide body of FIG. 2 taken from directional line 5-5.
Figure 9A:
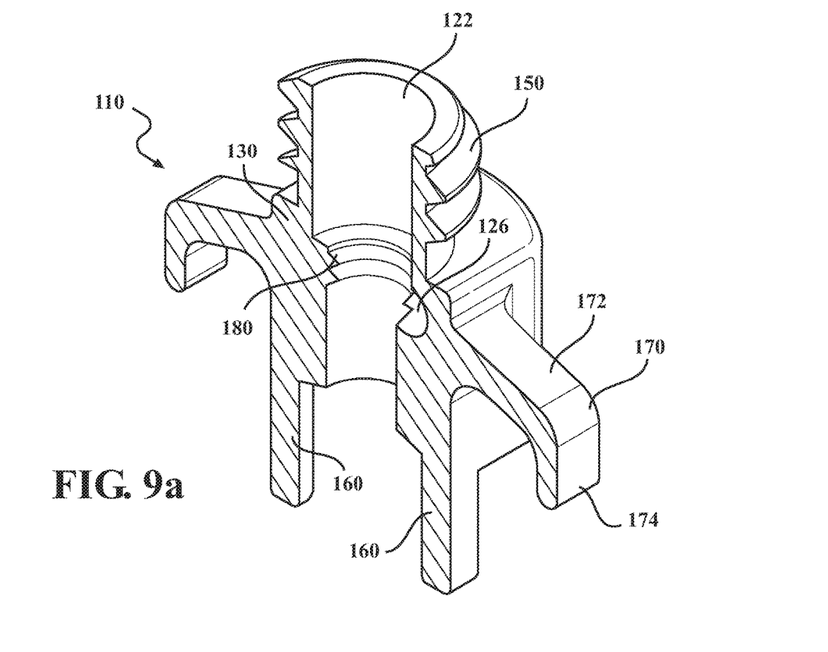
Figure 9B:
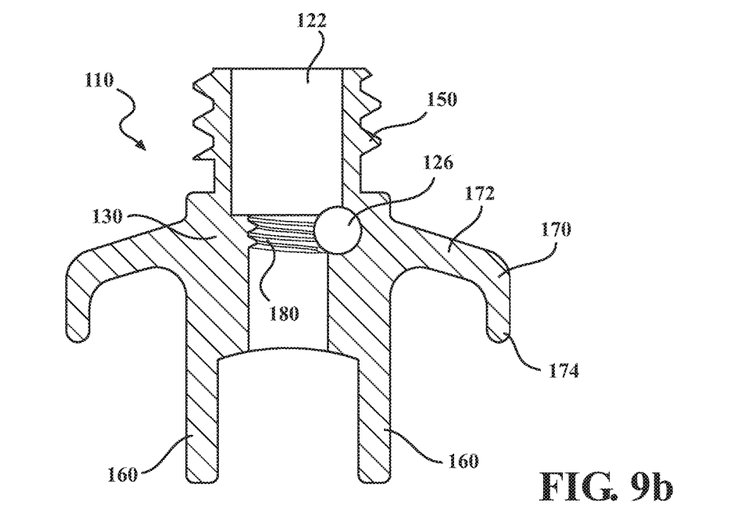

As shown in FIGS. 1-2, and 5, the body component 130 further comprises a proximal end 152 and a distal end 154. In some embodiments, the distal end 154 has curved surface configured to contact the surface of an interbody cage 200 coupled to the attachment guide 110. The distal end 154 may have a surface that is complementary to the surface of the interbody cage 200, as to optimize a flush contact engagement with the interbody cage 200. In many embodiments, the body component 130 further comprises an aperture 122 coaxially through the driver attachment element 150 and the distal end 154, wherein the aperture 122 is adapted to receive the screw 120. The body component 130 also comprises an aperture 126 through a thickness of the body component 130 and coupled with the aperture 122. The aperture 126 is adapted to receive the pin 124. The aperture 122 for the screw 120 is disposed along an axis 102 of the body component 130. The aperture 126 for the pin 124 is disposed orthogonal to the aperture 122 for the screw 120, such that the apertures 122 and 126 partially intersect (as illustrated in FIGS. 5 and 9a-b). When assembled, as shown in FIGS. 2 and 5, at least a portion of the pin 124 engages the screw 120, thereby capturing or securing the screw 120 within the body component 130. As illustrated in FIGS. 5 and 9a-b, the aperture 122 for receiving the screw 120 may further comprise an internal thread 180 for engaging the screw 120 to be disposed along the longitudinal axis 102.

A plurality of interbody cage engaging prongs 160 are disposed at the distal end 154 of the body component 130 and projecting from the distal end 154. The prongs 160 are configured to engage with openings 220 of the interbody cage 200 (see FIG. 3). In one embodiment, the prongs 160 may include a length that matches the thickness of the interbody cage 200, as to sufficiently engage the interbody cage 200. In many embodiments, the prongs 160 have a semi-cylindrical shape. In alternative embodiments, the prongs 160 may have square, triangular, rectangular, round, or other polygonal shapes, such shapes being adapted to mate with the openings 220 of the interbody cage 200. In some embodiments, the interbody cage 200 may further be coupled to the attachment guide 110 by means of the screw 120.

In some alternative embodiments, the interbody cage engaging prongs 160 may further comprise releasable clip elements or spring loaded ball detents. The clip elements or the spring loaded ball detents may be operated by an additional component of a driver assembly, which is configured to selectively release the clip elements or spring loaded ball detents from engagement with the interbody cage 200. In some alternative embodiments, the interbody cage engaging prongs 160 may be adapted to provide a frictional fitting between the openings 220 of the interbody cage 200 and the prongs 160. The frictional fitting may be released by the application of a sufficient force to separate the prongs 160 from the interbody cage 200 by the surgeon.

As shown in FIGS. 2 & 3, a plurality of plate receiving flanges 170 is disposed on the body member 130. The plate receiving flanges 170 are configured so as to receive an anterior cervical plate 300 having a central window 320 mated to the exterior surface of the body member 130 attachment guide 110. For example, the central window 320 may have the same profile as the exterior surface of the body member 130. In many embodiments, the flanges 170 are generally L-shaped, having an outwardly (from the body component 130) projecting portion 172 and a proximal to distal projecting lip 174. The flanges 170 may have curved or flat edge portions. The plate 300 is frictionally coupled to the flanges 170 in one embodiment, or alternatively, by a spring loaded ball detent. In use, a wall strut 322 forming the window 320 is disposed between the body component 130 and the flange 170 (see FIG. 3).

In some alternative embodiments, the plate receiving flanges 170 may further comprise releasable clip elements. The clip elements may be operated by an additional component of a driver assembly, which is configured to selectively release the clip elements from engagement with the plate 300. In some alternative embodiments, the plate receiving flanges 170 may be adapted to provide a frictional fitting between the window 320 of the plate 300 and the flanges 170. The frictional fitting may be released by the application of a sufficient force to separate the flanges 170 and plate 300 by the surgeon. Alternatively, hinged flanges may separate the plate 300.

Figure 6:
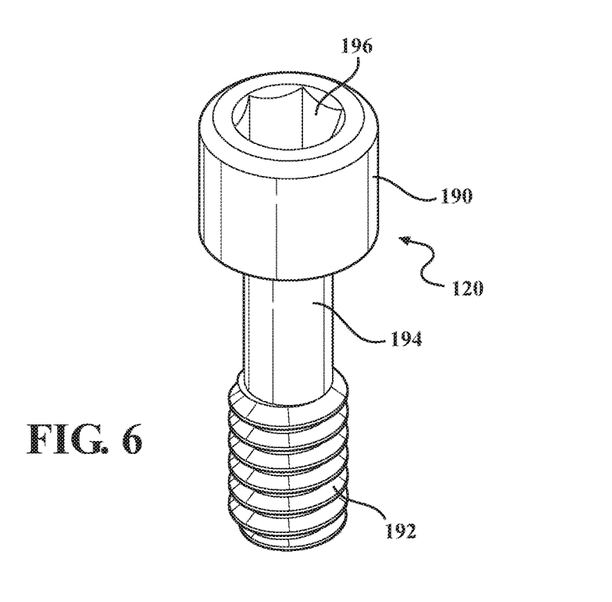
FIG. 6 is an isometric view of the screw for use with the attachment guide.

The screw 120 is illustrated in FIG. 6. The screw 120 generally comprises a head 190, a threaded distal end 192, and a smooth central portion 194. The smooth central portion 194 is adapted to interact with the body component 130 and the pin 124 to lock the screw 120 within the body component 130, as shown in FIG. 5. The head 190 of the screw 120 further comprises a drive bit receiving portion 196. In many embodiments, the drive bit receiving portion 196 is a hex drive system, but alternative receiving portions are contemplated within the scope of this disclosure, including but not limited to flat head slots, Phillips head slots, hexalobes, and/or the like. In use, the threaded distal end 192 of the screw 120 is driven through the internal threads 180 of the attachment guide 110, resulting in the smooth central portion 194 of the screw 120 being disposed in the threaded region 180 of the attachment guide 110, as shown in FIG. 5. The pin 124 is then inserted such that it is disposed along the smooth central portion 194 of the screw 120, thereby locking the screw 120 within the attachment guide 110. The threaded distal end 192 of the screw 120 may then be attached to the interbody 200 to hold the interbody 200 in a fixed association with the attachment guide 110.

Figure 4:
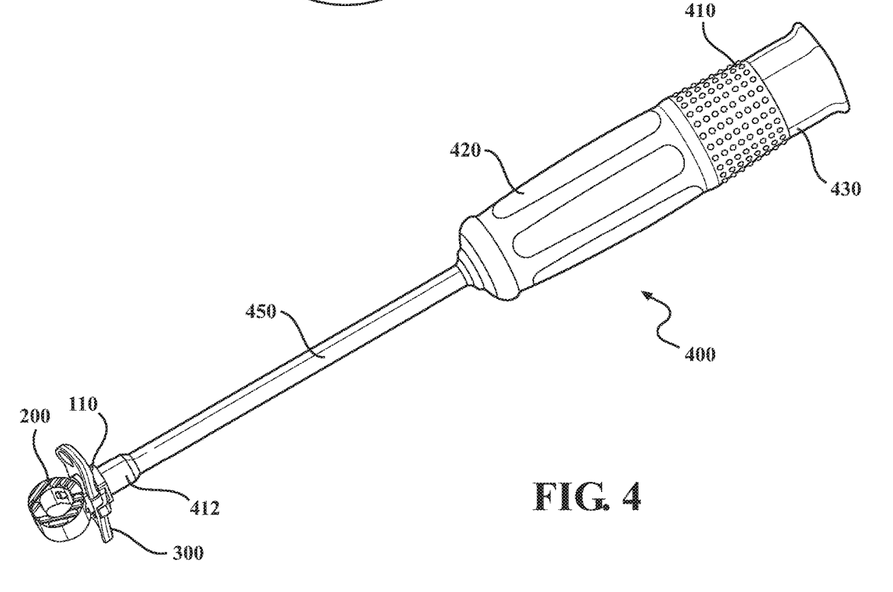
FIG. 4 is an isometric view of the attachment guide mated with an interbody cage and an anterior cervical plate, where the attachment guide is attached to a driver assembly.

As shown in FIG. 4, the attachment guide 110 may be attached to a driver assembly 400 for inserting the plate 300 and interbody 200 into the cervical spine disc space. In many embodiments, the body member 130 further comprises the driver attachment element 150 at the proximal end 152 of the body member 130. In some embodiments, the driver attachment element 150 comprises a threaded member disposed coaxially on the exterior surface of the driver attachment element 150. In many embodiments, the aperture 122 for receiving the screw 120 passes through the center of the driver attachment element 150. In some alternative embodiments, the driver attachment element 150 comprises a recess adapted to receive at least one selectively releasable clip element of the driver assembly 400, one or more prongs, a male element of a quick-attach system, and/or the like. Generally, the driver assembly 400 may be easily detached from the alignment guide 110 after the guide 110, interbody 200, and plate 300 are inserted into the cervical spine disc space. Once the driver assembly 400 is detached, a surgeon may drill, tap, and implant screws through the plate 300. Once the plate 300 is installed in the patient, the driver assembly 400 may be reattached to the guide 110, and the guide 110 removed from the patient, plate 300, and interbody 200. The plate 300 and interbody 200 are thus fully implanted and properly aligned with one another.

As shown in FIG. 4, the driver assembly 400 generally comprises an elongated outer shaft 450 having a distal end 412, and a handle 420 having a proximal end 410. In some embodiments, the distal end 412 further comprises a threaded component 414 configured to receive the driver attachment element 150 of the attachment guide 110. The threaded component may be detached from the driver attachment element 150 while the attachment guide 110 is inserted in the cervical spine disc space, such that a surgeon may have access to drill, tap, and implant screws through the plate 300. The threaded component may then be reattached to the driver attachment element 150 to permit removal of the attachment guide 110 from the cervical spine disc space. In some alternative embodiments, the distal end 412 may further comprise at least one selectively releasable clip element adapted to couple with recesses on the driver attachment element 150, prong receiving recesses, prongs, a female element of a quick-attach system, and/or the like.

Figure 7:
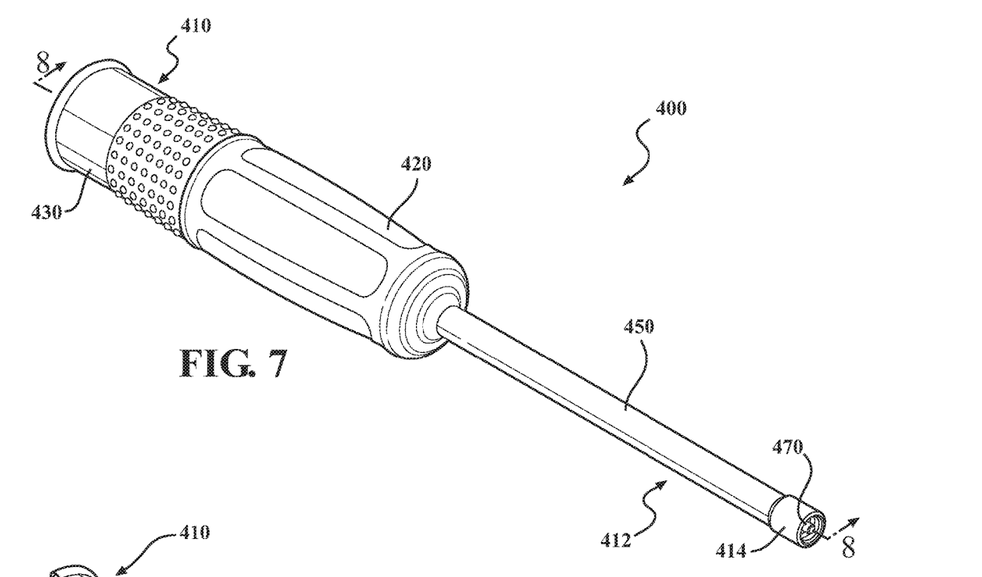
FIG. 7 is an isometric view of the driver assembly for use with the attachment guide.
Figure 8:
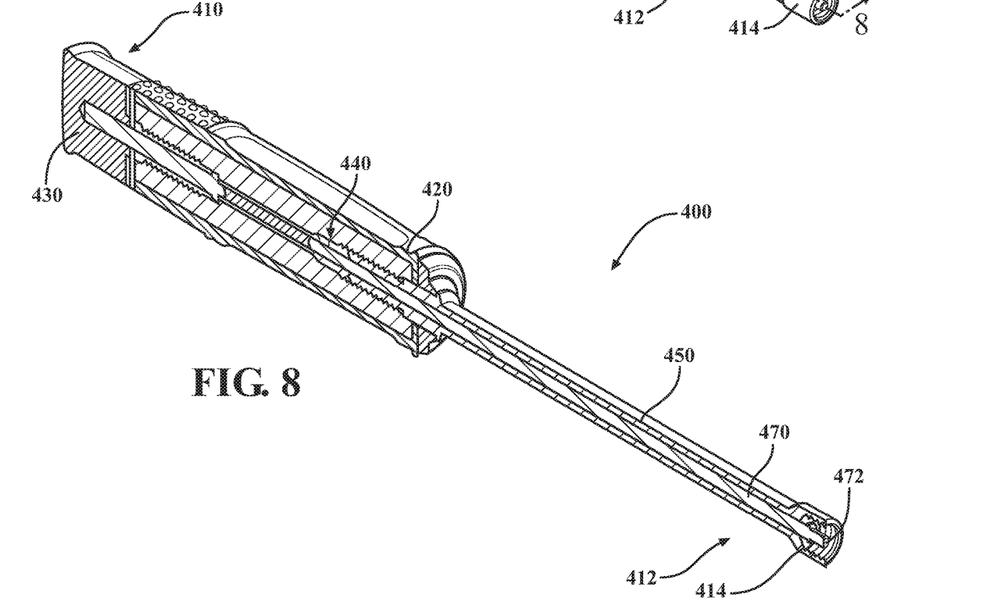
FIG. 8 is a cross sectional isometric view of the driver assembly for use with the attachment guide of FIG. 7 taken from directional line 8-8.

In some other embodiments, illustrated in FIGS. 7 and 8, the driver assembly 400 further comprises an aperture 440 disposed through the handle 420 and outer shaft 450. Disposed within the aperture 440 is an inner shaft 470 which has a drive bit 472 disposed at the distal end of the inner shaft 470. The drive bit 472 is configured to engage with the screw 120 and the drive bit receiving means 196 of the screw 120, when the driver assembly 400 is coupled to the attachment guide 110. The proximal end of the inner shaft 470 is fixedly coupled to an inner shaft handle 430, which is disposed proximal to the proximal end 410 of the handle 420. The inner shaft 470 is rotated by the inner shaft handle 430, independently of the handle 420 and outer shaft 450. The distal end 412 includes the threaded portion 414 to engage the threaded portion 150 on the body 130.

In some embodiments, the driver assembly 400 and attachment guide 110 may be combined into a single unit. Generally, the driver assembly 400 may be made from any suitable biocompatible material as known in the art including, by way of example and not limitation, stainless steel, silicone, shape memory materials, thermoplastic or other materials.

Figure 10A:
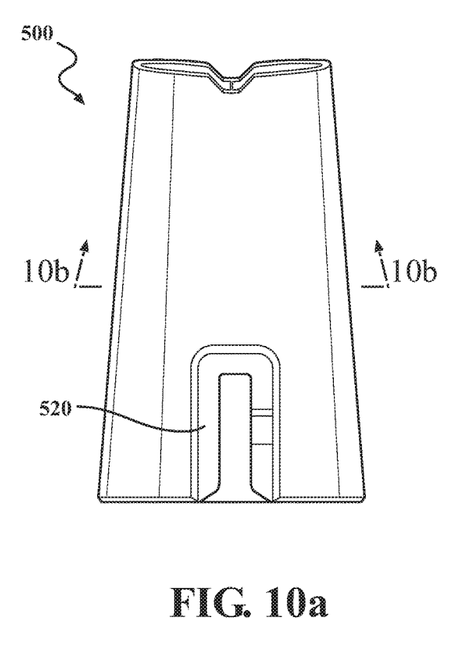
FIG. 10a is a front view of the drill guide component.
Figure 10B:
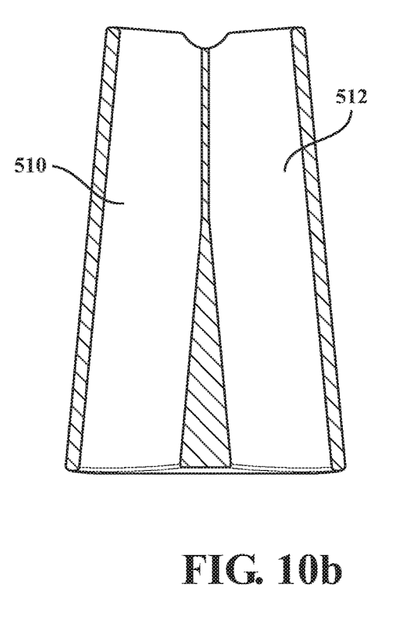
FIG. 10b is a front cross sectional view of the drill guide component of FIG. 10a taken from directional line 10b-10b.
Figure 10C:
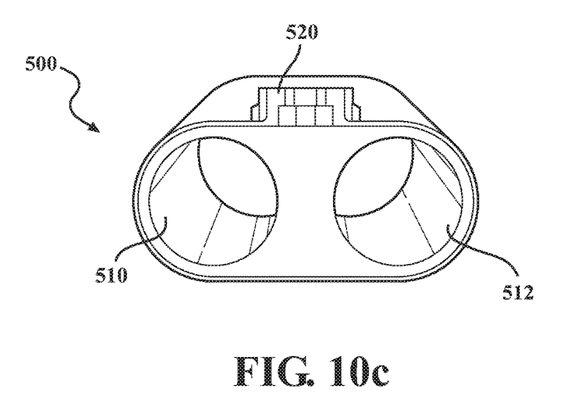

In some embodiments, at least one drill guide component 500 is provided to drill, tap, and implant screws into the cervical plate 300, as shown in FIG. 10a. The drill guide 500 generally includes an engagement portion 520 and at least two drilling lumens 510 and 512 traversing the length of the drill guide 500, as shown in FIGS. 10b and 10c. The drill guide 500 has a diameter configured to permit a drill bit to drill a set distance into the bone beneath the attachment guide 110, thereby preventing accidental drilling too deep by a surgeon implanting the interbody cage 200 and/or the plate 300. The engagement portion 520 includes a slotted feature that mates with the drill guide component 500.

Figure 11A:
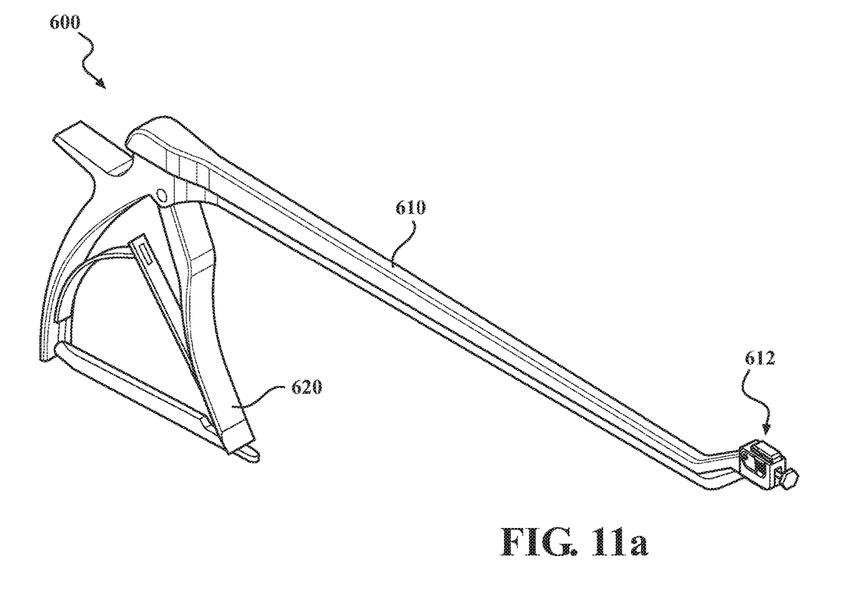
FIG. 11a is a perspective view of the holder.
Figure 11B:
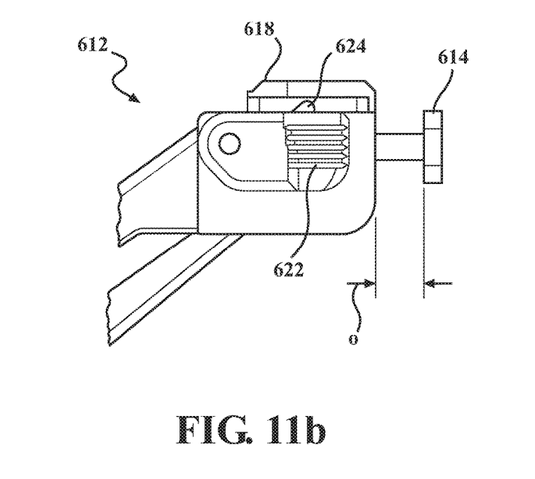
FIG. 11b is a side view of the distal holding portion with the spring loaded tip in an open state.
Figure 11C:
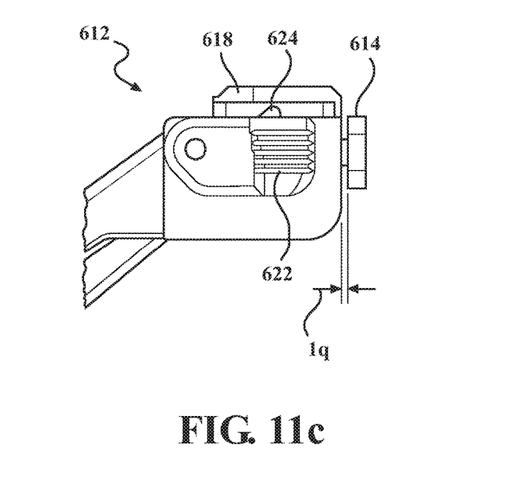
FIG. 11c is a side view of the distal holding portion with the spring loaded tip in a closed state.

The drill guide component 500 may be removably seated into a holder 600, as shown in FIG. 11a. The holder 600 includes a handle 620 operably coupled through a shaft 610 and a distal holding portion 612. As shown in FIGS. 11b and 11c, the distal holding portion 612 includes a spring loaded tip 614 that moves from an open state O to a closed state C upon operation of the handle 620, as to lock and hold the plate 300. A spring 622 is operably coupled with a tab 624 and the handle 620 to lock the spring loaded tip 614 in the open state O and closed state C. Operation of the handle 620 longitudinally moves the shaft 610 to displace the spring loaded tip 614. The distal holding portion 612 also includes a slotted clip 618 that mates with the slotted feature of the engagement portion 520 as to lock and hold the drill guide 500 in an orthogonal position relative to the plate 300.

In some embodiments, the attachment guide is a component of an attachment guide system comprising the attachment guide, an interbody cage, and an anterior cervical plate.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

Illustrated in FIGS. 1-5, an exemplary rod measuring instrument 100 includes a first indicating member 120a and a second indicating member 120b. The indicating members (collectively 120) may be substantially identical in features and components. For example, each indicating member 120 may further comprise a protractor member 125 and a shaft member 121. A measuring member 110 including a first end 111, a second end 112, and a length therebetween may link the indicating members 120. The protractor members (collectively 125) each include an aperture, slot, channel, or passageway for sliding engagement with the measuring member 110. The ends 111 and 112 may be adapted to prevent the removal of either or both indicating member 120a and 120b from the measuring member 110.

The measuring member 110 may include any of a variety of cross-sectional profiles including a d-rod, c-channel, cylindrical tube, square rod and the like. The measuring member 110 is marked with linear measurements along its length, such as in a millimeter scale or other alternative measurement scale. In the some examples, the linear measurements are marked on a flat surface of a d-rod shaped measuring member 110. Alternatively, the linear measurements may be marked along any desired portion of a surface of the measuring member 110. The length of the measuring member 110 is selected to permit measurement in a wide variety of surgical treatments, where at least two pedicle screws are utilized. In some embodiments, the measuring member 110 may be interchangeable.

In some examples, the indicating members 120 may both move along the measuring member 110. In other examples, such as in FIG. 1, the first indicating member 120a may be linearly fixed to the measuring member 110 at the first end 111, while maintaining pivotal freedom of the first shaft member 121a relative to the measuring member 110. The linear fixation of indicating member 120a to the measuring member 110 may be achieved by any of a variety of methods, including welding, a set screw, frictional force, glue, locking pins, clips, and/or the like. Non-permanent fixation methods may be advantageous, allowing the instrument 100 to be dismantled for ease of storage when not in use. The second indicating member 120b is movably coupled to the measuring member 110 through the aperture, so as to be capable of linear translation along the length of the measuring member 110. For both indicating members 120, pivotal freedom of the shaft 121 is obtained by a pivotal connection 109, which pivotally couples the shaft 121 to the protractor member 125. For example, the pivotal connection 109 may include a pin connecting the shaft 121 to the protractor member 125.

As shown in FIG. 5, the first and second shaft members 121 each have a distal end 122 adapted to be removably coupled to heads 205 of pedicle screws 200 in situ. The shaft members 121 may include a length to permit insertion through a surgical opening in a patient and extend away for ease of use by a surgeon. For example, the length may be substantially greater than a depth of the surgical site measured from the opening on the surface of the skin to the screw 200 within the vertebra. The length may be extendable. For example, the shaft member 121 may comprise a plurality of interchangeable shaft portions coupled together at couplings 124. The couplings 124 may include threaded, snap-fit, or other removable couplings to accommodate patient anatomy and surgeon preference. The first and second shaft members 121 further have a proximal end 123 adapted to be pivotally coupled to the protractor member 125. In another embodiment, the first and second shaft members 121 may have a height indicator (not shown), which lets a user know that the shaft member 121 is properly seated in the head of a pedicle screw. In another embodiment, the first and second shaft members 121 may further comprise one or more center beads 131, which maintain and stabilize the center of the shaft 121 relative to a tissue retractor previously installed in a patient's body The first and second protractor members 125 each comprise a body portion 126 and a needle 127. The body portion 126 may comprise a viewing port 128, through which the linear position of the protractor member 125 along the measuring member 110 can be determined. This viewing port 128 may be present on both protractor members 125 or on only one protractor member 125. The body portion 126 further comprises a measurement scale 129, which measures the deflection of the needle 127 by the shaft 121 as described herein. The measurement scale 129 may indicate either the angle of deflection a of the shaft 121 or a linear measurement which such angle of deflection represents. When the scale 129 indicates a linear measurement, the scale 129 may further indicate whether the measurement is additive or subtractive from the measurement indicated by the location of the indicating member 120 along the measuring member 110. For example, if a pedicle screw to which the first indicating member 120 is coupled lies beyond the first end 111 of the measuring member 110, then the displacement of the needle 127 along the scale 129 would indicate an additive linear measurement to the location of the first indicating member 120 along the measuring member 110, as measured through the viewing port 128. Alternatively, if the pedicle screw lies within the length of the measuring member 110, then the displacement of the needle 127 along the scale 129 would indicate a subtractive linear measurement.

The needle 127 may be directly coupled to or integral with the shaft 121, so as to cause the needle 127 to displace along the scale 129 as the shaft 121 is angularly deflected. In other examples, the first and second indicating members 125 may utilize a double-hinge assembly to convert small angular movements of the shaft members 121 into larger movements of the needles 127, so that small correction measurements may be accurately read. In the double-hinge embodiments, the needle 127 is pivotally coupled to the body portion 125, at a pivot. The needle 127 is then further pivotally coupled to the proximal end 123 of the shaft 121 by the double hinge assembly. Other known apparatus for amplifying smaller movements of the shafts 121 relative to the measuring member 110 may be used to improve accuracy.

As the shaft members 121 are coupled to the pedicle screws 200 at ends 122 (as shown in FIG. 5), the second indicating member 120 translates along the length of the measuring member 110 as necessary to allow the coupling of the second shaft member 121 and the pedicle screw head 205. The second indicating member 120 is located at a particular linear position along the length of the measuring member 110, such position indicating a particular linear measurement L along the measuring member 110, based on the linear separation of the first and second indicating members 120. The first protractor member 125 serves to convert an angular displacement of the first shaft member 121, and thus the linear displacement of the first pedicle screw, into a first measurement correction value L'. In a preferred embodiment, the first correction value is an additive or subtractive linear value (depending on the direction of angular displacement) in the same scale as the measuring member 110. In an alternative embodiment, the first correction value may only be an angular measurement, and require conversion by a user to a linear value. Similarly, the second protractor member 125 serves to convert the angular displacement of the second shaft member 121, and thus the linear displacement of the second pedicle screw, into a second measurement correction value L".

Once the linear measurement L, first correction value L', and second correction value L" are determined and converted to the same linear scale, the values may be summed to determine the necessary length of the stabilization rod. This length may natively include an arbitrary adjustment to allow for appropriate overhang length of the rod, or such arbitrary adjustment may be included by the user. The stabilization rod of appropriate length may be selected from pre-sized rods, or cut to size from stock rods.

In a further embodiment, the rod measuring instrument 100 may utilize electronic sensors to digitally determine and display the measurements of L, L', and L". The electronic elements may utilize any appropriate power source, such as a battery or an electrical outlet. In the above embodiments, the components of the rod measuring instrument 100 may be made of any medically suitable material, as known in the art. The shaft members 121 are preferably made of titanium for optimal imaging. Alternatively, the distal end 122 of the shaft 121 which makes contact with a pedicle screw head may comprise a material suitable for imaging, such as tantalum or gold.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An attachment guide for aligning an interbody cage and a spinal plate during insertion wherein the interbody cage and the spinal plate are separate and distinct, comprising:
   a proximal end including an inserter attachment element configured to removably receive an inserter instrument;
   a pair of flanges extending from the guide body configured to engage the spinal plate;
   a distal end including a surface configured to contact an anterior surface of the interbody cage and a cage engagement element configured to extend distally from the surface and into a wall of the interbody cage
   the guide body configured to simultaneously hold and align both the interbody cage and the spinal plate during insertion; and
   a coupling element extending through an aperture of the guide body from the proximal end to the distal end and configured to draw the pair of flanges into greater contact with the spinal plate and the cage engagement element into greater contact with the interbody cage.

2. The attachment guide of claim 1, further comprising a locking pin extending partially into the aperture and configured to engage the coupling element to prevent removal of the coupling element from the aperture.

3. The attachment guide of claim 1, wherein the inserter attachment element comprises an externally threaded projection.

4. The attachment guide of claim 1, wherein each of the pair of flanges includes a distal projecting lip configured to extend partially around a lateral portion of the spinal plate.

5. The attachment guide of claim 1, wherein the surface of the distal end is contoured to engage a curved anterior surface of the interbody cage.

6. The attachment guide of claim 1, wherein the cage engagement element comprises a pair of engaging prongs configured to extend into alignment apertures of the interbody cage.

7. The attachment guide of claim 1, wherein the aperture for receiving the coupling element is disposed along a longitudinal axis of the guide body and a second aperture is disposed orthogonal to and partially intersecting the first aperture, such that when the screw and a locking pin are inserted into the first and second apertures the screw is captured within the body component by the locking pin.

8. The attachment guide of claim 1, wherein the screw further comprises a head portion, a smooth central portion, and a threaded portion.

9. The attachment guide of claim 1, in combination with an inserter instrument comprising:
   an outer shaft including a distal end configured to engage the inserter attachment element and a proximal end with a first handle portion to attach the inserter instrument to the attachment guide; and
   an inner shaft extending through the outer shaft and including a distal end configured to engage the coupling element and a proximal end with a second handle portion to actuate the coupling element.

10. The attachment guide of claim 9, wherein the distal end of the outer shaft comprises an internal thread and the distal end of the inner shaft comprises a drive bit.

11. An attachment guide for aligning an interbody cage and a spinal plate during insertion, comprising:
   a guide body including:
      a proximal end including an externally threaded projection configured to removably receive an inserter instrument;
      a pair of flanges extending from the guide body configured to extend partially around a lateral portion of the spinal plate;
      a distal end including a contoured surface configured to contact an curved anterior surface of the interbody cage and a cage engagement element comprising a pair of engaging prongs configured to extend distally from the surface and into alignment apertures in a wall of the interbody cage;
      the guide body configured to simultaneously hold and align both the interbody cage and the spinal plate during insertion; and
   a coupling element extending through an aperture of the guide body comprising a proximal head portion with a drive bit recess, a smooth central portion, and a threaded distal portion configured to threadably engage the wall of the interbody cage; and a locking pin extending partially into the aperture and configured to engage the smooth central portion of the coupling element to prevent removal of the coupling element from the aperture.

12. The attachment guide of claim 11, wherein actuation of the coupling element draws the pair of flanges into greater contact with the spinal plate and the pair of engaging prongs into greater contact with the interbody cage.

13. The attachment guide of claim 11, in combination with an inserter instrument comprising:
   an outer shaft including a distal end configured to engage the inserter attachment element and a proximal end with a first handle portion to attach the inserter instrument to the attachment guide; and
   an inner shaft extending through the outer shaft and including a distal end configured to engage the coupling element and a proximal end with a second handle portion to actuate the coupling element.

14. The attachment guide of claim 13, wherein the distal end of the outer shaft comprises an internal thread and the distal end of the inner shaft comprises a drive bit.

15. A system for pre-aligning a spinal plate with an interbody cage during insertion, comprising:
   an alignment guide including
      a guide body with a proximal end including an externally threaded projection, a pair of flanges extending from the guide body configured to extend partially around a lateral portion of the spinal plate, and a distal end including a contoured surface configured to contact an curved anterior surface of the interbody cage and a cage engagement element comprising a pair of engaging prongs configured to extend distally from the surface and into alignment apertures in a wall of the interbody cage;
   a coupling element extending through an aperture of the guide body comprising a proximal head portion with a drive bit recess, a smooth central portion, and a threaded distal portion configured to threadably engage the wall of the interbody cage;

a locking pin extending partially into the aperture and configured to engage the smooth central portion of the coupling element to prevent removal of the coupling element from the aperture;

the guide body configured to simultaneously hold and align both the interbody cage and the spinal plate during insertion; and an inserter instrument including:

an outer shaft including a distal end with an internal thread to engage the externally threaded projection and a proximal end with a first handle portion to attach the inserter instrument to the attachment guide; and an inner shaft extending through the outer shaft and including a distal end with a drive bit to engage the drive bit recess and a proximal end with a second handle portion to actuate the coupling element.

* * * * *